(12) United States Patent
Sitther et al.

(10) Patent No.: US 10,793,883 B2
(45) Date of Patent: Oct. 6, 2020

(54) ENGINEERED CYANOBACTERIA WITH ENHANCED LIPID PRODUCTION

(71) Applicant: Morgan State University, Baltimore, MD (US)

(72) Inventors: Viji Sitther, Pikesville, MD (US); Somayeh Gharaie Fathabad, Parkville, MD (US)

(73) Assignee: Morgan State University, Baltimore, MD (US)

( * ) Notice: Subject to any disclaimer, the term of this patent is extended or adjusted under 35 U.S.C. 154(b) by 0 days.

(21) Appl. No.: 16/123,484

(22) Filed: Sep. 6, 2018

(65) Prior Publication Data
US 2019/0071699 A1 Mar. 7, 2019

Related U.S. Application Data

(60) Provisional application No. 62/555,119, filed on Sep. 7, 2017.

(51) Int. Cl.
| | |
|---|---|
| *C12P 7/64* | (2006.01) |
| *C07K 14/195* | (2006.01) |
| *C12N 1/20* | (2006.01) |
| *C12N 15/74* | (2006.01) |
| *C12N 9/00* | (2006.01) |
| *C12R 1/01* | (2006.01) |
| *C12N 9/02* | (2006.01) |

(52) U.S. Cl.
CPC ............ *C12P 7/649* (2013.01); *C07K 14/195* (2013.01); *C12N 1/20* (2013.01); *C12N 9/0071* (2013.01); *C12N 15/74* (2013.01); *C12P 7/6463* (2013.01); *C12R 1/01* (2013.01); *C12Y 114/19* (2013.01)

(58) Field of Classification Search
None
See application file for complete search history.

(56) References Cited

U.S. PATENT DOCUMENTS

| | | | | |
|---|---|---|---|---|
| 2009/0203070 A1* | 8/2009 | Devroe | ............... | C12N 9/1007 435/69.1 |
| 2016/0097029 A1* | 4/2016 | Sitther | ............... | C07K 14/195 435/134 |

OTHER PUBLICATIONS

Santos et al., "Combinatorial engineering of microbes for optimizing cellular phenotype", Curr. Op. Chem. Biol., 2008, vol. 12, pp. 168-176.*

Fathabad et al., "Augmenting Fremyella diplosiphon Cellular Lipid Content and Unsaturated Fatty Acid Methyl Esters via Sterol Desaturase Gene Overexpression", Applied Biochemistry and Biotechnology, Dec. 2019, vol. 189, No. 4, pp. 1127-1140.*

* cited by examiner

*Primary Examiner* — Suzanne M Noakes

(74) *Attorney, Agent, or Firm* — Whiteford, Taylor & Preston, LLP; Peter J. Davis

(57) ABSTRACT

A recombinant strain of *F. diplosiphon* was made by transforming wild type *F. diplosiphon* with a pGEM-7Zf (+) plasmid containing sterol desaturase gene (SD) via electroporation. The recombinant strain was designated B481-SD and overexpressed the sterol desaturase gene to result in enhanced lipid production. Selection made on NaCl enabled growth of the transformant to thrive up to 50 g $L^{-1}$ NaCl. This strain was designated B481-SDH.

2 Claims, 12 Drawing Sheets
Specification includes a Sequence Listing.

| Gene | Sterol desatuarse |
|---|---|
| Size (bp) | 1314 |

Transformant

Wild-type

SEQUENCE LISTING

<160> NUMBER OF SEQ ID NOS: 1

<210> SEQ ID NO 1
<211> LENGTH: 1314
<212> TYPE: DNA
<213> ORGANISM: Fragaria vesca

<400> SEQUENCE: 1

```
ttgacttttg acttcttcat agcgggacta gcgctgataa aaaccgagta cagaaaaatt      60
acgatgaatg ttttagcaca aagctgggct gagattgcgg ctcaattaca gataaattgg     120
aatctggtaa atacctgctt gcagtttgct agttggggat tagtctcgct gttgttggta     180
gagatagtga gagatagcta tcatgctttg tgtcactatg tcccctcgct tggtaaatgg     240
cataataagc accacatggc gtatcgccgc gatttatcgg tagtttcttt aaaaatttac     300
caagagtctc agttatacaa tgatattgtc gagtcaacgc tactggttgt agttttgact     360
gtgatggctt tactgctaca gcaatggggc ttttggttgg gagtagtcta tgctttcacc     420 ttttatatg gcgcgtcccg gcgatatttt ctcggtaaaa ttgatacaga ttacactcac     480
ctccccgggc cattagaaac tattccctcg gtttggtggg taaatcgttc ttaccactgg     540
cgacatcatt ttgatgatgt taacgcctat tacagtggtg tgtttccttt agtagatacg     600
gtattgggaa caggtttatc tcttaaaggt aaaaccattg ctttaactgg tgcttccggt     660
gctttagggc aagcattgac tgctgaattg attaaaaata atgccaaggt agtagcctta     720
actaccaatc ccgaaaaact acagcctcaa gaaaagctaa ctgtaattgc ttgggaattg     780
ggtaaggaag cagagttaaa agctgcttta gagaaagttg atattttgat tatcaatcac     840
ggtgtcaatg tctacgctaa ccgcacctca gaagcaattg agtcttctta tgaggtgaat     900 acttttttcta cattgcggtt gatggatata ttttttggcaa ccgttaccgg gccgcaatcc     960
aaagcaacta agaaatttg ggttaacact tccgaagctg aagtatctcc ggctttaagt    1020
cctctttatg aactcagtaa acgcgctatc ggagatattg ttaccctcaa gcgtttggat    1080
ggggattgta taattcgcaa gttaattctg ggccgtttta agagtcaact taatccttat    1140
ggggtgatgt cagcgccgca agtagcccgt gcaattttgt ttttagcaaa gcgggacttc    1200
```

```
cgcaatatta ttgtgtccat caatcccctg acatatctgc tgtttccgtt gaaggaagtt      1260
agcacttggc tttactaccg aatctttagt aaaaaggttc aatctttgaa ctaa            1314
```

ENGINEERED CYANOBACTERIA WITH ENHANCED LIPID PRODUCTION

FIELD OF THE INVENTION

The present invention relates to compositions and methods for increasing the lipid production of cyanobacteria.

DESCRIPTION OF THE BACKGROUND

The need and the market for microorganism propagation technology has expanded dramatically in the last decades with more and more "bioproducts" being produced experimentally and even commercially using specially engineered microorganisms. One important class of bioproducts is lipids. Lipids are naturally occurring molecules that include fats, waxes, sterols, fat-soluble vitamins (such as vitamins A, D, E, and K), monoglycerides, diglycerides, triglycerides, phospholipids, and others.

Fatty acids (FAs) are a major component of lipids that determine important membrane properties such as viscosity and permeability. FA structure is determined by the chain length (number of carbon atoms) and number of double bonds in these chains. In cyanobacteria, the FA chain length usually varies from C14 to C18 and the number of double bonds vary from 0 to 4 providing fully saturated FAs (with no double bonds), monoenoic (with 1 double bond), dienoic (with two double bonds) and polyunsaturated fatty acids (PUFAs) that contain two or more double bonds in their backbone. Double bonds are introduced into the hydrocarbon chains of FA by fatty acid desaturase enzymes. PUFAs are applied for global research because of their nutritional value, medicinal applications, and potential use in biofuel production.

Lipids are typically contained in photosynthetic bacteria and algae in the form of membrane components, storage products, and metabolites. Certain algal strains, particularly microalgae such as diatoms, certain chlorophyte species, and bacteria such as cyanobacteria, contain proportionally high levels of lipids. In cyanobacteria, PUFAs are mainly present in the thylakoid membranes and have a significant effect on biofuel production. Algal sources for the algae oils can contain varying amounts, e.g., from 2 wt % to 40 wt % of lipids, based on total weight of the biomass itself.

Other bioproducts include biopolymers, nutraceuticals (e.g., vitamins) and pharmaceuticals; such as antimicrobials, antivirals, antifungals, neuroprotectives.

Another bioproduct is "biofuel," which includes fuel derived from biomass conversion. This renewable source of energy significantly contributes to energy security and alleviates the harmful effects of particulates, carbon monoxide and hydrocarbons in diesel-powered vehicles. With the negative impact of fossil fuel on the environment, it is more important than ever to find alternative sources of energy. Biofuel derived from cyanobacteria and algae has replaced around 1 billion gallons of petroleum diesel. These organisms convert light energy into chemical energy through photosynthesis. Since cyanobacteria provide very high levels of net energy, converting biomass into fuel is much less energy-intensive than other methods of conversion.

A recent analysis showed that current water and land resources in the U.S. could support the production of as much as 23.5 billion gallons/year (BGY) of algae-based fuel. The study also projected the number could be increased by 78.2 BGY (or 2.5 billion barrels/year) from biofuel production in saline waters. The U.S. Navy alone uses 36.5 million barrels of oil per year. It has mandated that 50% of its energy needs will be from domestic renewable fuel by 2020 as part of its national security strategy and it is investing heavily in the biofuel industry. The biofuel industry is expanding and is expected to double over the next 10 years into a $185 billion industry.

Engineered cyanobacteria have attracted attention as catalysts for the direct conversion of carbon dioxide into biofuel. Genetic manipulation techniques have been well-established in cyanobacteria which have made this organism a highly tractable platform to build efficient biosynthetic pathways for biofuel production. Transformation techniques including methods to introduce DNA into cells, suitable promoters, and expression vectors are developed to increase total lipid content and reduce the cost of microalgal diesel production. In transformation, promoters have significant roles in successful gene expression due to their ability to regulate expression of a transgene. A number of transformation techniques have been used to transfer DNA to cyanobacterial cells including electroporation, artificial transposons, viruses, and *Agrobacterium*-mediated transformation. Transformation of lipid production genes such as Δ12 desaturase, Δ9 desaturase and Δ15 desaturase genes have been reported to enhance the unsaturation of membrane lipids and thereby improve the tolerance of *Synechococcus* sp. PCC 7942 and *Synechocystis* sp. PCC6803 strains to intense light.

The freshwater cyanobacterium, *Fremyella diplosiphon*, is a model cyanobacterial species which has great potential as a commercial biofuel agent due to its fast generation time, ability to grow in low light intensity, and impressive response to macronutrient deprivation. In addition, *F. diplosiphon* regenerates light-dependent changes in pigmentation and morphology during complementary chromatic acclimation (CCA) to efficiently harvest available radiant energy for photosynthesis.

Recently, the inventors genetically transformed the wild type strain of *F. diplosiphon* for enhanced salt tolerance. The transformant is described in U.S. application Ser. No. 15/833,870, the entirety of which is incorporated herein by reference. The halotolerant strain is now capable of growing in marine water with an average concentration of 35 g/L NaCl. In addition, the inventors discovered that nano- and micro-particles, when complexed to bioproduct-producing and biomass/biofuel photosynthetic microorganisms, can increase both the growth rate and the photosynthetic efficiency of the microorganism, as compared to non-complexed microorganisms. These complexes are described in U.S. application Ser. No. 15/678,643, the entirety of which is incorporated herein by reference.

SUMMARY OF THE INVENTION

The present inventors have discovered a solution for generating an alternative source of biofuel from cyanobacteria in saline water, which is otherwise unsuitable for irrigating crops or for any other purpose. Novel recombinant cyanobacteria, *F. diplosiphon*, having enhanced lipid production and halotolerance is provided. Gene candidates for lipid enhancement were isolated, sequence analyzed and at least one gene candidate was incorporated into plasmids which were used to transform wild type *F. diplosiphon* to develop a genetically transformed cyanobacteria strain with increased sterol desaturase (SD) expression and enhanced lipid production. Integration of the SD gene was confirmed with RT-qPCR, and physiological evaluations were conducted.

The present invention arises from the development by the inventors of a transformed strain of *F. diplosiphon* that successfully overexpresses a SD gene to result in enhanced lipid production. Sterol desaturase is responsible for lipid production, having a wide range of enzyme activities and functions in lipid metabolism. Enzymes of this superfamily catalyze NADPH-dependent reactions. More specifically, the inventors developed a pGEM-7Zf (+) plasmid containing SD gene which was used to transform wild type (WT) *F. diplosiphon* B481 strain via electroporation to result in a transformant designated as B481-SD.

Total RNA in *F. diplosiphon* was extracted, cDNA reverse transcribed, and the genes amplified by PCR. Purified amplified cDNA were subjected to Sanger sequencing and NCBI Basic Local Alignment Sequence Tool analysis performed to confirm identity of the genes and encoded proteins. Results revealed open reading frames of 1314 base pairs encoding 437 for sterol desaturase. Sequence alignment revealed a 94% to sterol desaturase in *F. diplosiphon*, thus confirming the identity of the gene.

Recombinant strains of *F. diplosiphon* produced by the methods of the present invention include strain designated B481-SD. The sterol desaturase gene expressed by B481-SD is characterized by the sequence of SEQ.ID.NO. 1, which sequence was submitted to NCBI GenBank, National Center for Biotechnology Information, National Library of Medicine, Building 38A, Bethesda, Md. 20894 with under accession number #MH329183 on May 10, 2018.

The transformant B481-SD showed a 64-fold increase in mRNA transcript level. Gravimetric analysis revealed a 27.3% increase in total lipid content of the transformed strain relative to WT. Gas chromatography-mass spectrometry(GC-MS) revealed a 23% increase in desirable unsaturated fatty acid methyl esters (FAMEs) in B481-SD transesterified lipids, with methyl octadecenoate (C18:1) and methyl octadecadienoate (C18:2) as the most abundant desaturated components. Two-dimensional gas chromatography with time-of-flight mass spectrometry of transesterified lipids identified C12:0, C15:0, C18:3, and C18:4 components which were not previously detected in 1D GC-MS. Results of the study indicated that overexpression of the SD gene increased total lipid content as well as essential unsaturated fatty acids that maximize the potential of *F. diplosiphon* as a large-scale biofuel agent.

Overexpression of SD gene enhances salt stress tolerance indicated by growth of the transformant (B481-SD) even up to 50 g/l NaCl. It appears that excess desaturation decreases rigidification of membranes leading to reduced damage by salt stress.

Accordingly, there is presented according to one embodiment of the invention, a recombinant cyanobacterium having increased lipid production.

The recombinant cyanobacterium can be made by using conventional molecular methods known in the art. For example, the recombinant cyanobacterium can be made by introducing a polynucleotide encoding a sterol desaturase gene into wild-type cyanobacterium. The polynucleotide encoding a sterol desaturase gene can also be integrated into the genome of the cyanobacterium in order to make a recombinant cyanobacterium.

The present invention also relates to compositions comprising a recombinant cyanobacterium produced by methods described herein. The compositions described herein may include a carrier or excipient suitable for the recombinant cyanobacterium. Non-limiting examples include, but are not limited to, buffered saline, seawater, and BG-11 media and combinations thereof.

Another aspect of the invention is related to a method for producing a recombinant cyanobacterium characterized by increased lipid production as compared to wild-type cyanobacterium. The method includes introducing a polynucleotide encoding sterol desaturase gene into the cyanobacterium to produce a recombinant cyanobacterium having increased lipid production capability.

In one embodiment, the method for producing a recombinant cyanobacterium with increased lipid production capability further includes a step of incorporating at least one polynucleotide encoding a sterol desaturase gene in one or more plasmids and a step of integrating the polynucleotide encoding a sterol desaturase gene into the genome of the cyanobacterium.

The present invention uses standard methods for transformation of prokaryotes known in the art. (Berger, S. L. and Kimmel, A. R. (1987), Guide to Molecular Cloning Techniques, Methods in Enzymology Vol. 152, Academic Press, Inc., San Diego, Calif.; Sambrook, et al. (1989), Molecular Cloning—A Laboratory Manual (2nd ed.) Vol. 1-3, Cold Spring Harbor Laboratory, Cold Spring Harbor Press, N.Y.; and Current Protocols in Molecular Biology, F. M. Ausubel. et al., eds., Current Protocols, a joint venture between Greene Publishing Associates, Inc. and John Wiley & Sons, Inc., (through and including the 1997 Supplement), which are hereby expressly incorporated by reference in their entireties).

Non-limiting examples of transformation techniques that may be used in the present invention include, but are not limited to, direct incubation in the presence of exogenous DNA, transformation by heat-shock, transformation by electroporation, transformation by biolistic particle bombardment, transformation via addition of fusogenic agents (i.e., polyethylene glycol), conjugation with a heterologous microorganism, or transduction via viral particles.

The method according to this aspect of the invention can further include a step of isolating or making a polynucleotide encoding a sterol desaturase gene and incorporating the nucleic acid in one or more plasmids. The method can further include a step of integrating the recombinant nucleic acid into the genome of the cyanobacterium.

Another aspect of the invention relates to a plasmid containing a polynucleotide encoding a sterol desaturase gene. The plasmid construct is such that it is capable of being transformed into a cyanobacterium.

Plasmids relevant to genetic engineering typically include at least two functional elements 1) an origin of replication enabling propagation of the DNA sequence in the host organism, and 2) a selective marker (for example an antibiotic resistance marker conferring resistance to ampicillin, kanamycin, zeocin, chloramphenicol, tetracycline, spectinomycin, and the like). Plasmids are often referred to as "cloning vectors" when their primary purpose is to enable propagation of a desired heterologous DNA insert. Plasmids can also include cis-acting regulatory sequences to direct transcription and translation of heterologous DNA inserts (for example, promoters, transcription terminators, ribosome binding sites); such plasmids are frequently referred to as "expression vectors." When plasmids contain functional elements that allow for propagation in more than one species, such plasmids are referred to as "shuttle vectors." Shuttle vectors are well known to those in the art.

The present invention also relates to compositions comprising one or more plasmid(s) or expression vector(s) described herein. The compositions described herein may include a carrier or excipient suitable for the plasmid(s) or expression vector(s). Non-limiting examples include, buffered saline, seawater, and BG-11 media, and combinations thereof.

In some embodiments, one or more other genes of interest may be inserted into the cyanobacterium. Each gene of interest may be expressed on a unique plasmid or expressed as part of a single plasmid. In preferred embodiments, the desired biosynthetic pathways are encoded on multi-cistronic plasmid vectors. Useful expression vectors are designed internally and synthesized by external gene synthesis providers.

Another aspect of the invention relates to a method of producing biofuel using the recombinant cyanobacteria of the present invention. The method includes growing the recombinant cyanobacteria comprising at least one nucleotide encoding a sterol desaturase gene under conditions suitable for production of lipids for said biofuel production, and isolating the lipid.

According to other embodiments of the invention, the microorganism may be a bioproduct producing microorganism. According to various sub-embodiments, the microorganism may produce lipids selected from the group consisting of fats, waxes, sterols, fat-soluble vitamins (such as vitamins A, D, E, and K), monoglycerides, diglycerides, triglycerides, and phospholipids.

According to further embodiments of the invention, the microorganism may be a bioproduct producing microorganism producing a bioproduct selected from the group consisting of biopolymers, nutraceuticals and pharmaceuticals, wherein the pharmaceuticals include antimicrobials, antivirals, antifungals, and neuroprotectives.

Unless defined otherwise, all technical and scientific terms used herein have the meaning commonly understood by a person skilled in the art to which this invention belongs

DETAILED DESCRIPTION OF THE INVENTION

1. Methods and Materials 1.1. Strain and Culture Conditions

*F. diplosiphon* strain B481 was used as the wild type for transformation. Cultures were grown in liquid BG-11 medium containing 20 mM HEPES (hereafter referred to as BG-11/HEPES) at 170 rpm and 28° C. for seven days under continuous white light adjusted to 30 µmol $m^{-2}s^{-1}$ using the model LI-190SA quantum sensor (Li-Cor, USA). Escherichia coli FB5a competent cells (Thermo Fisher Scientific, USA) were grown at 37° C. in Luria-Bertani (LB) broth or agar plates containing 80 mg $L^{-1}$ ampicillin as the selective antibiotic.

1.2. Extraction of Complementary DNA

Total RNA was extracted from *F. diplosiphon* B481 strain at an optical density of 0.6 at 750 nm ($OD_{750}$) using Tri Reagent (Molecular Research Center, Inc., USA) according to the manufacture protocol. The quantity and quality of extracted RNA were verified using electrophoresis on agarose gels stained with GelRed (Phenix Research, USA) and A260/280 spectrophotometric ratio. Complementary DNA (cDNA) was reverse transcribed using high capacity RNA to cDNA (Life Technologies, USA).

1.3. PCR Screening and Sequencing of *F. diplosiphon* Sterol Desaturase Gene

Homologs of the lipid production sterol desaturase gene were identified in *F. diplosiphon*. PCR amplification was performed with 50 ng cDNA using a C1000 Touch Thermocycler (Bio-Rad, USA). Primers designed to amplify the genes contained a HindIII restriction site added to the 5' ends and BamHI to the 3' ends. PCR products electrophoresed on a 1.2% agarose gel (FIG. 1) were excised at the expected size ranges and cDNA bands extracted using the Gel Recovery kit (Zymo Research, USA). Amplified fragments were sequenced using ABI 3130 XL Genetic Analyzer (Life Technologies, USA) and chromatograms were analyzed using Finch TV Version 1.4.0 (Geospiza Inc., USA). Basic Local Alignment Sequence Tool (BLAST) and BLASTx analysis were performed to confirm the homology of the genes. Sequences were compared to the NCBI nucleotide collection database to determine the percentage of identity relative to homologous genes in other species and submitted to GenBank.

1.4. Construction of Expression Plasmids

Figure 2:
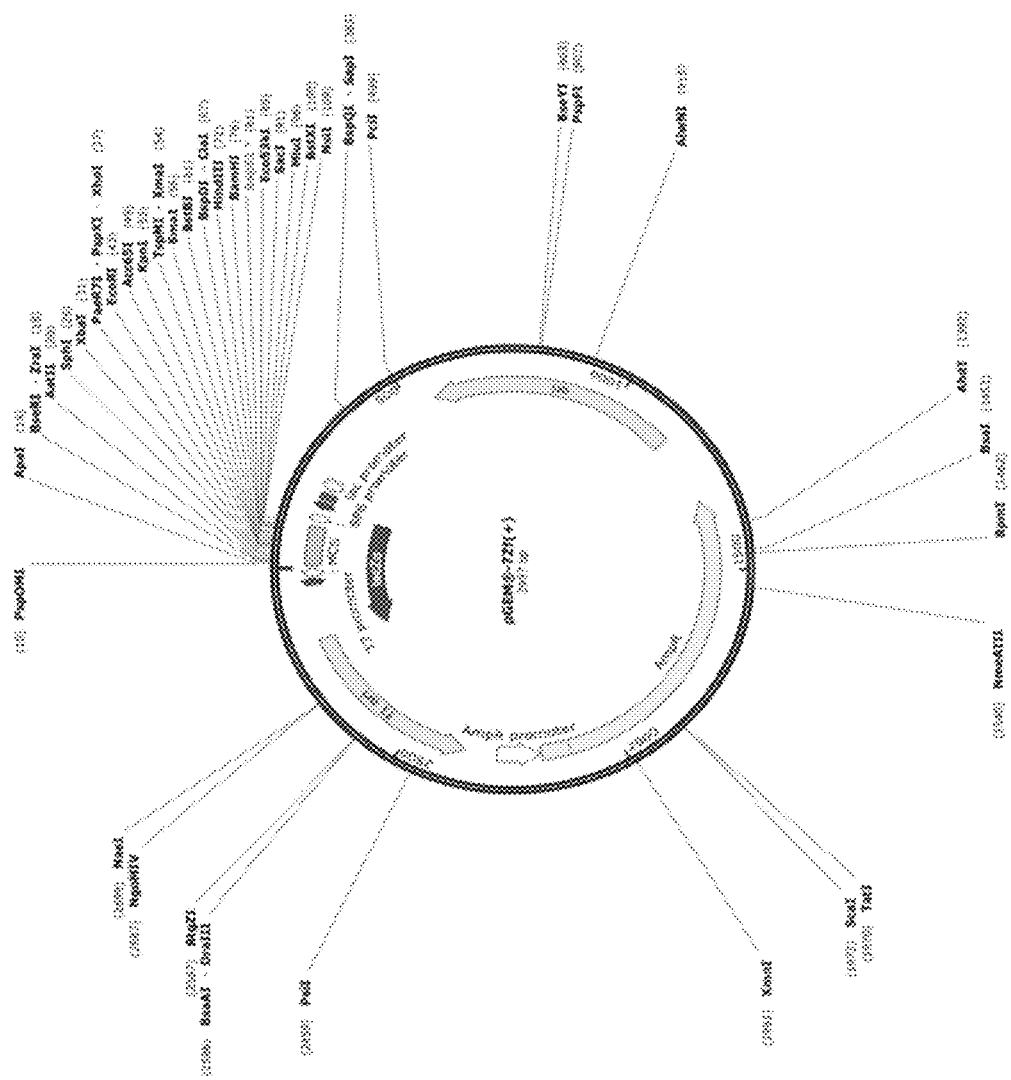
FIG. 2 is a representation of the plasmid pGEM-7Zf.

Expression plasmids pGEM-7Zf-SD (FIG. 2) with native promoters were constructed to overexpress the sterol desaturase gene. Amplified gene product was double digested with HindIII, BamHI, and pGEM-7Zf (+) vector (Promega, USA) was triple digested with HindIII, BamHI and ScaI enzymes and bands extracted. Purified inserts were cloned and ligated into the vector with T4 DNA ligase (NEB, USA) at the corresponding restriction sites. Plasmids were transformed into E. coli FB5u competent cells (Thermo Fisher Scientific, USA) via heat shock at 42° C. for 20 s and incubated in super optimal broth with catabolite repression media at 37° C. for 1 h (Thermo Fisher Scientific, USA). Transformed competent cells were plated on LB agar plates containing 80 mg $L^{-1}$ ampicillin and incubated for 16 h at 37° C. Resistant colonies were selected and grown overnight in liquid LB medium containing ampicillin. Plasmids were extracted from transformed cells and checked for the presence of the insert by PCR and further confirmed by triple digestion and sequence analysis.

1.5. Electroporation-Mediated Transformation

Expression plasmids harboring the sterol desaturase gene were transformed into wild type *F. diplosiphon* using electroporation as described by Kehoe and Grossman. Cultures were grown in BG-11/HEPES to an optical density at 750 nm ($OD_{750}$) of 0.5 under continuous white light at 15 µmol $m^{-2}s^{-1}$ followed by 72 hours in dark at 170 rpm. After centrifugation at 3450×g for 10 min, the pellet was washed thrice with distilled water and the supernatant removed. Concentrated cells (40 µl) were mixed with 6 µg purified plasmid DNA on ice and electroporated using a GenePulser Xcell (Bio-Rad, USA) at 200Ω resistance, 1.0 kV, and 25 g capacitance. After incubation on ice for 20 min, cells were grown in 10 ml BG11/HEPES liquid cultures for 16 h and transferred to BG-11/HEPES solid plates supplemented with 80 mg $L^{-1}$ ampicillin for selection of electrotransformants. Stability of sterol desaturase in the transformants was confirmed by weekly subculture on 80 mg $L^{-1}$ ampicillin for over 28 generations.

1.6. PCR Analysis of Transformed Strains

To verify the insertion of the sterol desaturase gene, we performed PCR with primers specific for this gene. Amplifications were performed in a 50 µl, reaction volume containing 25 µl of 2×KOD Hot Start Master Mix (EMD Millipore, USA), 1.5 µl each of 10 µM forward and reverse primers, 50 ng template cDNA and nuclease free water. PCR amplifications were performed as mentioned above and products visualized on a 1.2% agarose gel with a GeneRuler 100 bp plus ladder.

1.7. RNA Extraction and cDNA Synthesis

Total RNA in WT and B481-SD was extracted and cDNA synthesized according to the manufacture's protocol.

1.8. Quantification of *F. Diplosiphon* Gene Expression Levels Using RT-qPCR Reverse Transcription-quantitative PCR (RT-qPCR) was used to quantify gene overexpression in the transformant. Real-time amplifications performed using SYBR green master mix (Applied Biosystem, USA). A Thermal Cycler CFX96 Real Time machine (Bio-Rad, USA) was used to perform RT-qPCR. The reaction was performed in 20 µl volume containing 10 µl SYBR Master Mix, 10 ng cDNA template. Amplifications were performed under the following conditions: 95° C. for 20 s; 95° C. for 20 s; and 40 cycles of 95° C. for 30 s. Four replicates were maintained for each treatment type and relative quantification (RQ) data of the wild type and transformant was analyzed using the ΔCt method with CFX Manager 3.1 (Bio-Rad, USA).

1.9. Culture of Transformant in 80 mg $L^{-1}$ Ampicillin

The transformant was cultured in liquid BG-11/HEPES media containing 80 mg $L^{-1}$ ampicillin over a ten day-period under conditions described above. WT grown in the absence of ampicillin served as control. Culture conditions were maintained as described above and growth ($OD_{750}$) measured every 24 h using a Cynmar 1105 spectrophotometer (Cynmar, USA). B481-SD was grown in BG11/HEPES media containing 80 mg $L^{-1}$ ampicillin over 20 generations.

1.10. Analysis of Transformant's Photosynthetic Efficiency

Photosynthetic efficiency of the transformant was examined by extraction and quantification of chla and phycobiliproteins and compared to the wild type. For estimation of chla, absorption spectra of WT and transformant were measured at $A_{665}$ while for phycobiliproteins quantified at $A_{565}$, $A_{620}$ and $A_{650}$.

1.11. Lipid Production Analysis

Total lipid contents in WT and B481-SD *F. diplosiphon* was determined using a chloroform:methanol extraction method based on Folch, et al. reported in Wahlen, et al. Dried samples (80-100 mg) were sonicated in 5 mL of chloroform:methanol (2:1 by volume) for 30 s and centrifuged at 6000 rpm, washed with 1 mL distilled water, and centrifuged at 2000 rpm to facilitate phase separation. Methanol and sulfuric acid partitioned with water in the upper phase, while lipids separated with chloroform in the lower phase. The organic phase was transferred into a new tube and extraction was repeated twice to collect residual lipids. The organic phase was transferred into pre-weighted flasks followed by drying in a rotary evaporator and weighed to determine lipid yield of each sample. Three biological replicates were maintained and the experiment repeated once. Significance among cumulative treatment means was determined using ANOVA and Tukey's honest significant differences post hoc test at 95% confidence intervals ($P<0.05$). The single factor, fixed-effect ANOVA model, $Yij=\mu+\alpha Si+\varepsilon ij$, was used where Y is the total lipid yield content in strain i and biological replicate j. The µ represents overall total lipid content mean with adjustments from the effects of strain ($\alpha S$), and εij is the experimental error from genotype i and biological replicate j.

1.12 Gas Chromatography-Mass Spectrometry of Transesterified Product for FAME Analysis:

We determined FAME composition of transesterified material using a Shimadzu GC17A/QP5050A GC-MS combination (Shimadzu Instruments, USA) at the Mass Spectrometry Facility at Johns Hopkins University (Baltimore, Md.). The GC17A was equipped with a low-polarity (5% phenyl-, 95% methyl-siloxane) capillary column (30 m length, 0.25 mm ID, 0.25 µm film thickness, and 10 m length guard column). We identified peaks by comparing mass spectra to The Lipid Web Archive of FAME Mass Spectra. Three biological replicates of each sample were analyzed, and the experiment repeated once. In addition, we also calculated theoretical chemical and physical properties of the transesterified lipids from FAME composition (w %) using BiodieselAnalyzer© software Version 2.2.

1.13 GC×GC-TOFMS analysis of total transesterified lipids

High-resolution GC×GC-TOFMS from LECO (USA) was used to identify FAMEs from the WT and B481-SD strains. Total lipids were extracted, subjected to direct transesterification as explained above, dried under dry $N_2$ (g), and reconstituted in 2 mL dichloromethane with cholestane (50 µg $mL^{-1}$) spiked as an internal standard.

1.14 Growth of Transformant in Increasing NaCl Concentrations

Growth of the transformant and wild type were evaluated in BG11/HEPES containing various concentrations of NaCl. B481-SD was cultured in 250 ml conical flasks containing 100 ml liquid BG-11/HEPES media at NaCl concentrations ranging from 10 to 50 g $L^{-1}$ over a ten day-period under conditions described above.

1.15. RNA Extraction and cDNA Synthesis

Total RNA of the halotolerant strain (B481-SDH) was extracted and cDNA synthesized according to the manufacturer's protocol.

1.16. Quantification of B481-SDH Gene Expression Levels Using RT-qPCR

SD gene overexpression in B481-SDH was quantified using RT-qPCR. Real-time amplifications were performed using SYBR green master mix (Applied Biosystem, USA) as mentioned above.

2. Results

2.1. Identification of Sterol Desaturase Homologues in *Fremyella Diplosiphon*

Figure 1:
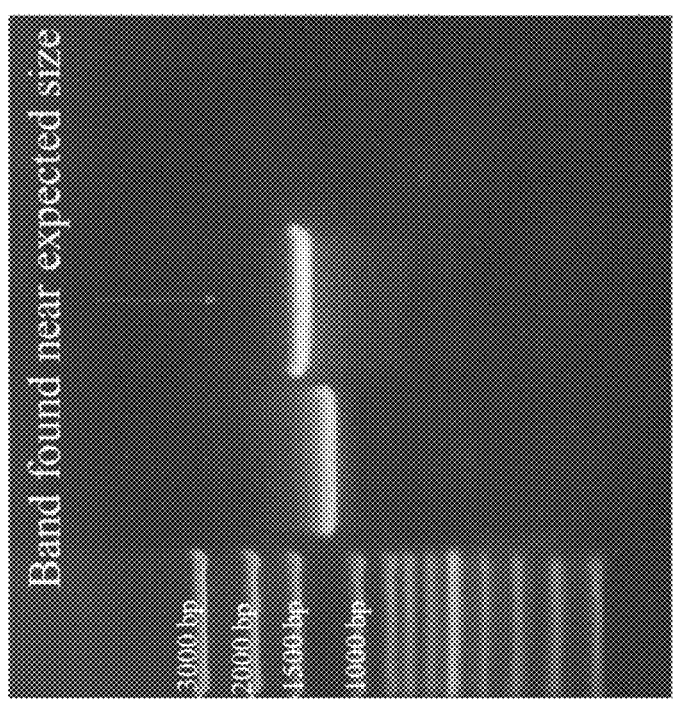
FIG. 1 is a representation of the identification of the sterol desaturase gene.

Primer-specific amplification of *F. diplosiphon* revealed a single discrete band at the expected size of 1314 base pairs for the SD gene (FIG. 1). Purified products were successfully subjected to Sanger sequencing and NCBI BLAST analysis to confirm identity of the SD gene and its encoded proteins. Results of this study revealed an open reading frame of 1314 base pairs encoding 437 amino acids for the SD protein. The sequence alignment identified a 94% match to SD gene in *F. diplosiphon*, thus confirming the identity of the gene. The amino acid sequence of SD revealed 93%, 86%, 77%, and 77% identities to *Nostoc carneum* NIES-2107, *Calothrix* sp. NIES-2100, *Nodularia* sp. NIES-3585, and *Fortiea contorta* respectively. The SD sequence was deposited at NCBI Genbank with the accession number MH329183.

2.2. Cloning and Transformation of Sterol Desaturase Gene in *F. Diplosiphon*

Figure 3:
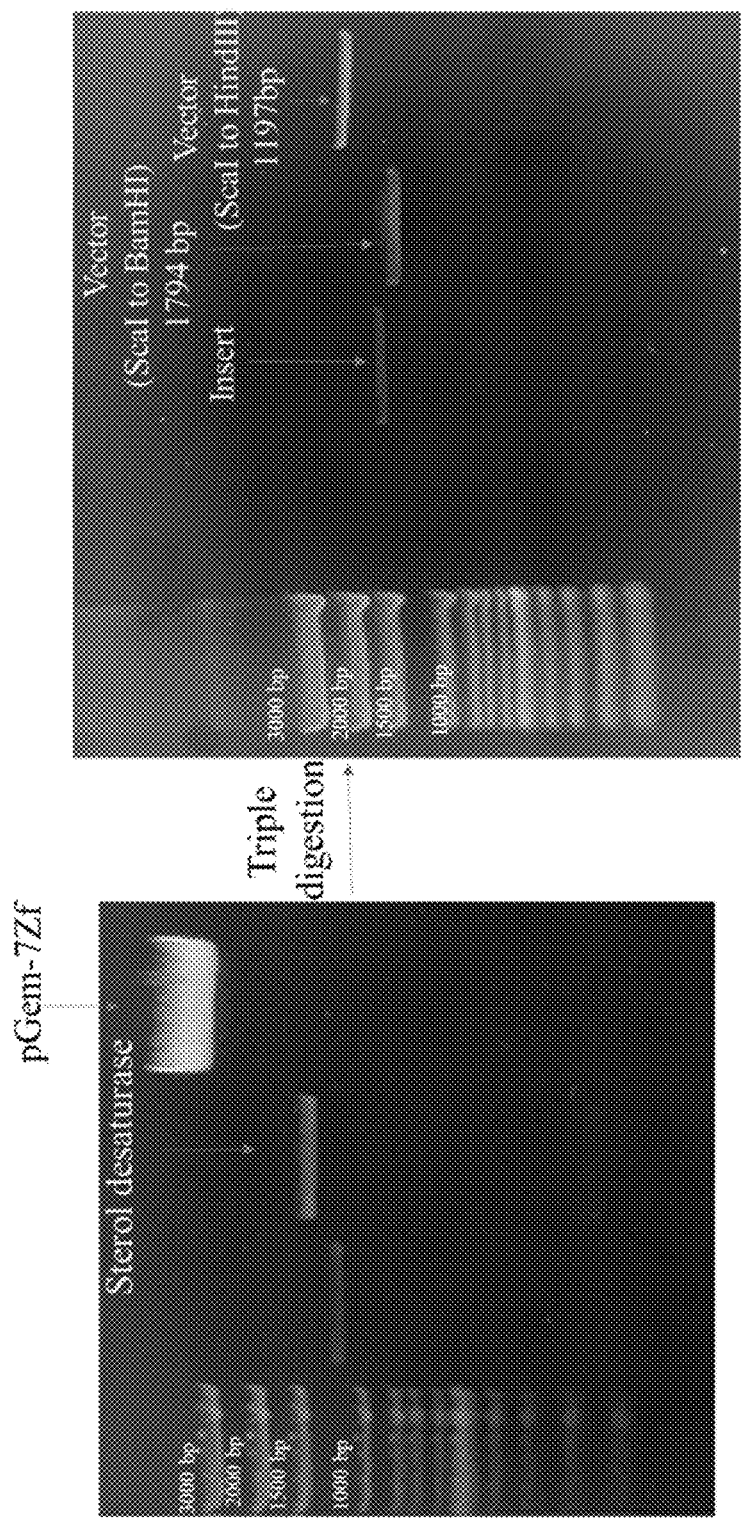
FIG. 3 shows electrophoresis of pGEM-7Zf-SD plasmid after triple digestion.

Amplified products and pGEM-7Zf (+) vector were double and triple digested using HindIII, BamHI, and ScaI followed by ligation of purified inserts into the vector at the corresponding restriction sites (FIG. 3). pGEM-7Zf-SD plasmid containing the SD gene was constructed, cloned, and transformed into WT via electroporation. Gene insertion was confirmed by primers specific to the SD gene and Sanger sequencing. The resultant SD-expressing *F. diplosiphon* strain was designated B481-SD.

Figure 4:
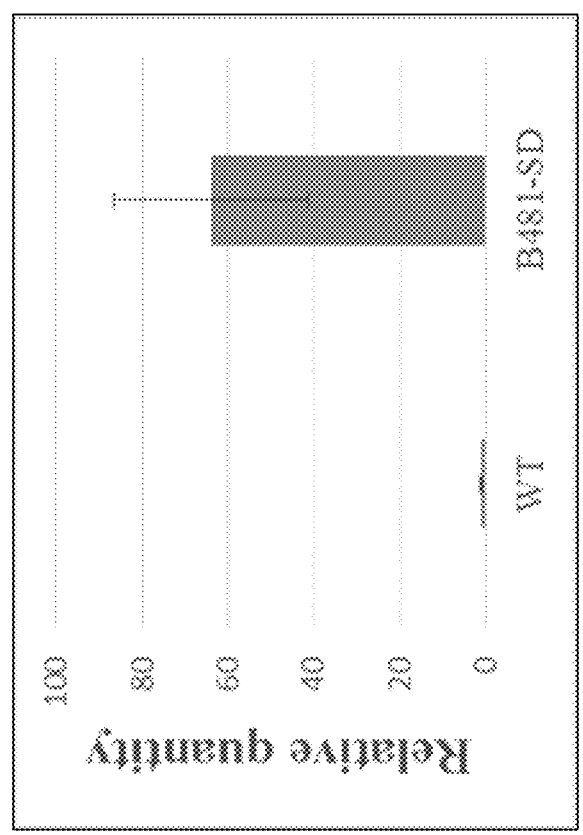
FIG. 4 shows the relative quantification of sterol desaturase transcript levels of the wild type (WT) and transformed strain (B481-SD).

2.3. RT-qPCR Analysis Confirms Overexpression of Sterol Desaturase in B481-SD A significant increase in mRNA transcript level was detected in *F. diplosiphon* transformant. Relative quantity values revealed a 64-fold increase in expression of SD gene in B481-SD compared to WT (FIG. 4).

Figure 5:
FIG. 5 shows wild type B481 and transformant B481-SD grown on BG11 media containing 80 mg $L^{-1}$ ampicillin.
Figure 5:
Figure 6:
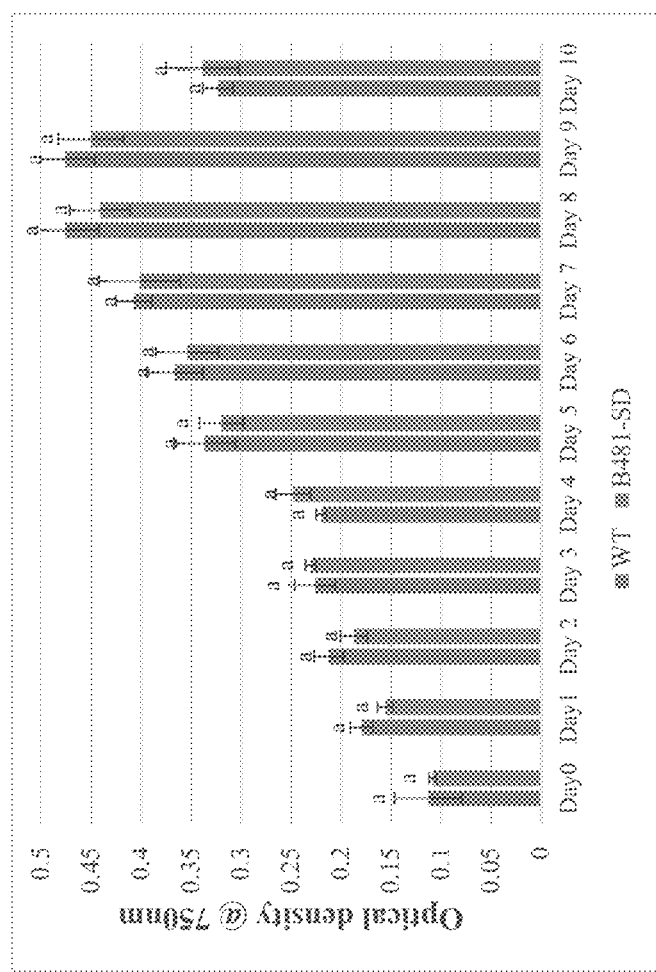
FIG. 6 shows the growth of *Fremyella diplosiphon* wild type (WT) and transformant (B481-SD) in BG11/HEPES medium over a ten day-period.
Figure 7:
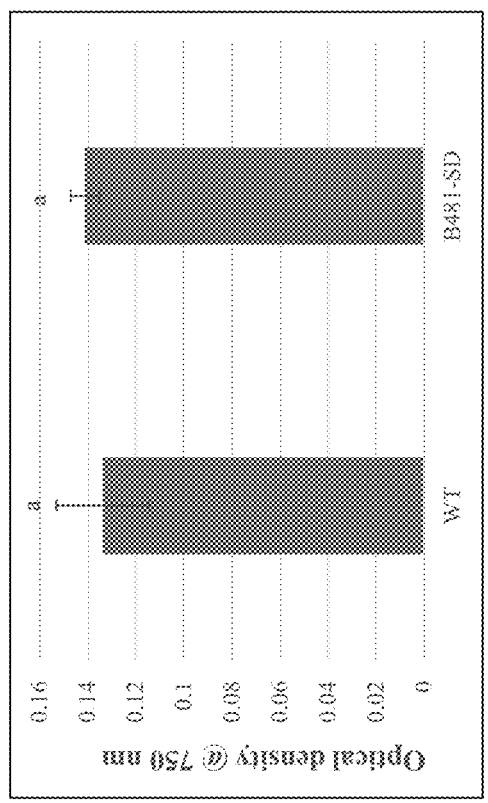
FIG. 7 shows the effect of sterol desaturase gene overexpression on growth rates of *Fremyella diplosiphon* wild type (WT) and transformant (B481-SD).

2.4 Validation of Transformant Growth and Photosynthetic Pigment Accumulation in Ampicillin Media No significant difference was observed in growth and growth rate of B481-SD in liquid BG-11/HEPES medium containing 80 mg $L^{-1}$ ampicillin (FIGS. 5-7). B481-SD was persistently grown in BG11/HEPES media containing 80 mg $L^{-1}$ ampicillin over 28 generations.

Figure 8:
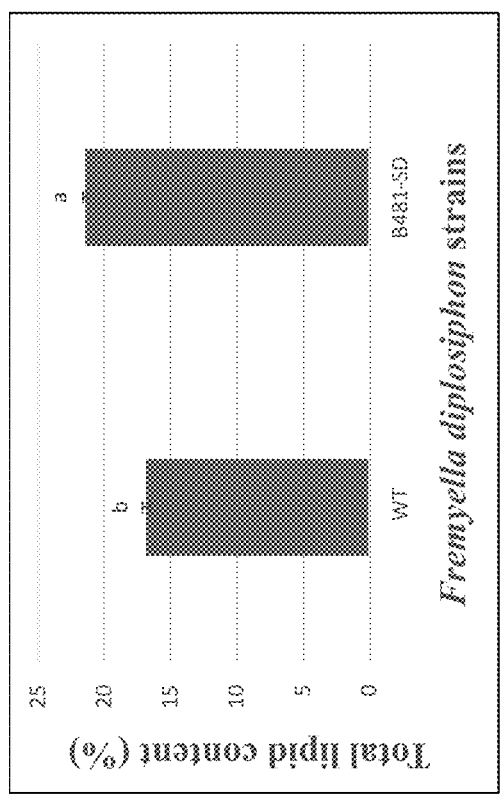
FIG. 8 shows the comparison of total lipid content in wild type (WT) and transformant (B481-SD) *Fremyella diplosiphon*.

2.5 Determination of Total Lipid Content in Transformant Strain by Gravimetric Analysis Results of gravimetric analysis revealed a significant increase in B481-SD total lipid yield compared to the WT (FIG. 8). While a total lipid content of 17% cellular dry weight (CDW) was detected in the wild type, 23% CDW lipid yield was quantified in the transformant. Thus, a 27% increase in total lipid was observed in B481-SD relative to SVT.

2.6 Characterization of FAME in Wild Type and Transformant Strain by GC-MS

We identified methyl palmitate, the methyl ester of hexadecanoic acid (C16:0) as the most abundant FAME, which accounted for 76.35% and 65.93% of total FAMEs produced from WT and B481-SD total lipids respectively (Table 1).

Table 1 shows breakdown of saturated and unsaturated fatty acid methyl ester (FAME) proportions in wild type (WT) and transformant (B481-SD) *Fremyella diplosiphon*.

TABLE 1

| Strain | FAME Type (%) | | Ratio of FAME |
|---|---|---|---|
| | Saturated | Unsaturated | Saturated/Unsaturated |
| WT | 80.99 | 19.01 | 4.26 |
| B481-SD | 76.62 | 23.38 | 3.27 |

In addition to methyl palmitate, other FAMEs including methyl tetradeconate (C14:1), methyl hexadecenoate (C16:1), methyl octadecanoate (C18:0), methyl octadecenoa to (C18:1), and methyl octadecadienoate (C18:2) were identified (Table 2).

Table 2 shows composition of fatty acid methyl ester in transesterified lipids of *Fremyella diplosiphon* wild type (WT) and transformant (B481-SD) strains.

TABLE 2

| | WT | | | | B481-SD | | | |
|---|---|---|---|---|---|---|---|---|
| | :0[b] | :1 | :2 | SUM | :0 | :1 | :2 | SUM |
| C14[a] | — | 3.07 | — | 3.07 | — | 3.21 | — | 3.21 |
| C16 | 72.39 | 11.66 | — | 84.05 | 65.67 | 7.67 | — | 73.34 |
| C18 | 8.60 | 1.79 | 2.49 | 12.88 | 10.95 | 5.16 | 7.34 | 23.45 |
| SUM | 80.99 | 16.52 | 2.49 | 100 | 76.62 | 16.04 | 7.34 | 100 |

[a]Column represents length of carbon chain.
[b]Row represents degree of saturation (number of double bonds in chain).

Figure 9:
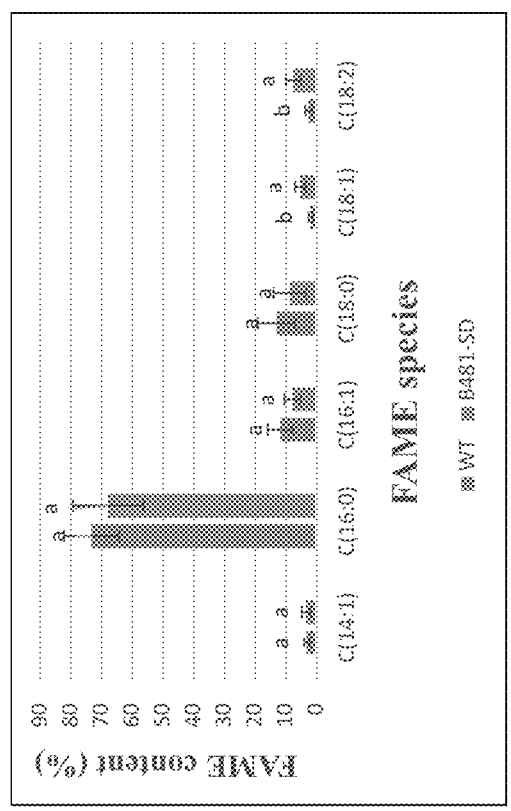
FIG. 9 shows fatty acid methyl ester (FAME) composition of wild type (WT) and transformant (B481-SD) *Fremyella diplosiphon* total lipids subjected to direct transesterification.

Results of the study revealed significant increases in methyl octadecenoate (C18:1), and methyl octadecadienoate (C18:2) levels from B481-SD transesterified lipids, while no significant differences were observed in other components obtained from *F. diplosiphon* transesterified lipids (FIG. 9).

2.7 Lipid Characterization in Transformant Strain by GC×GC-TOFMS

Figure 10:
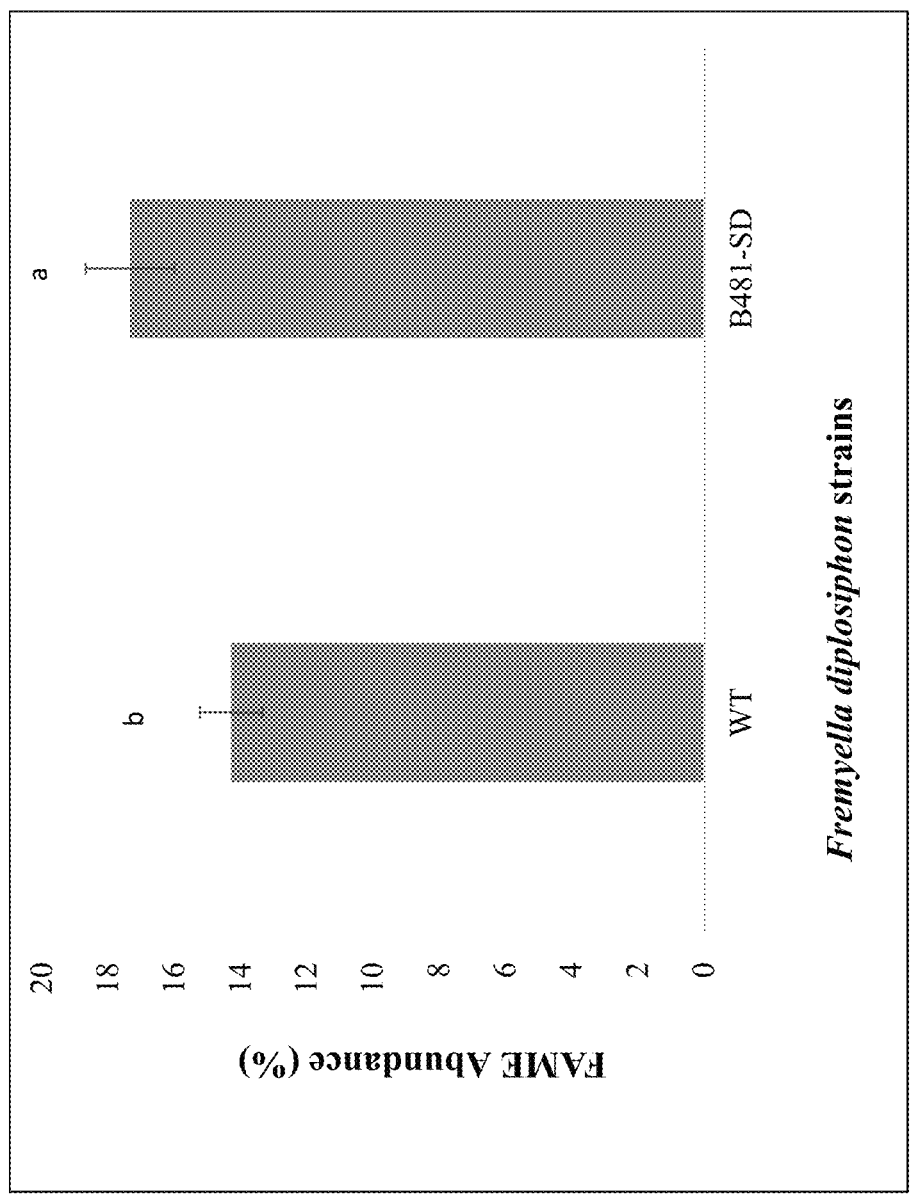
FIG. 10 shows fatty acid methyl ester (FAME) abundance in transesterified extractable lipids of wild type (WT) and transformant (B481-SD) *Fremyella diplosiphon* determined using GC×GC-TOFMS.

GC×GC-TOFMS analysis revealed the presence of FAMEs with carbon number from 12-18, as well as alkanes from C11 to C34. However, FAME abundance in B481-SD (80.92% TL) was significantly higher than WT (77.92% TL) (FIG. 10). Our results revealed FAME compounds such as C12:0 C15:0, C18:3, and C18:4 identified by GC×GC-TOFMS which were not detected in 1D GC-MS.

2.8. Transformed Strain Exhibit Enhanced Halotolerance

Figure 11:
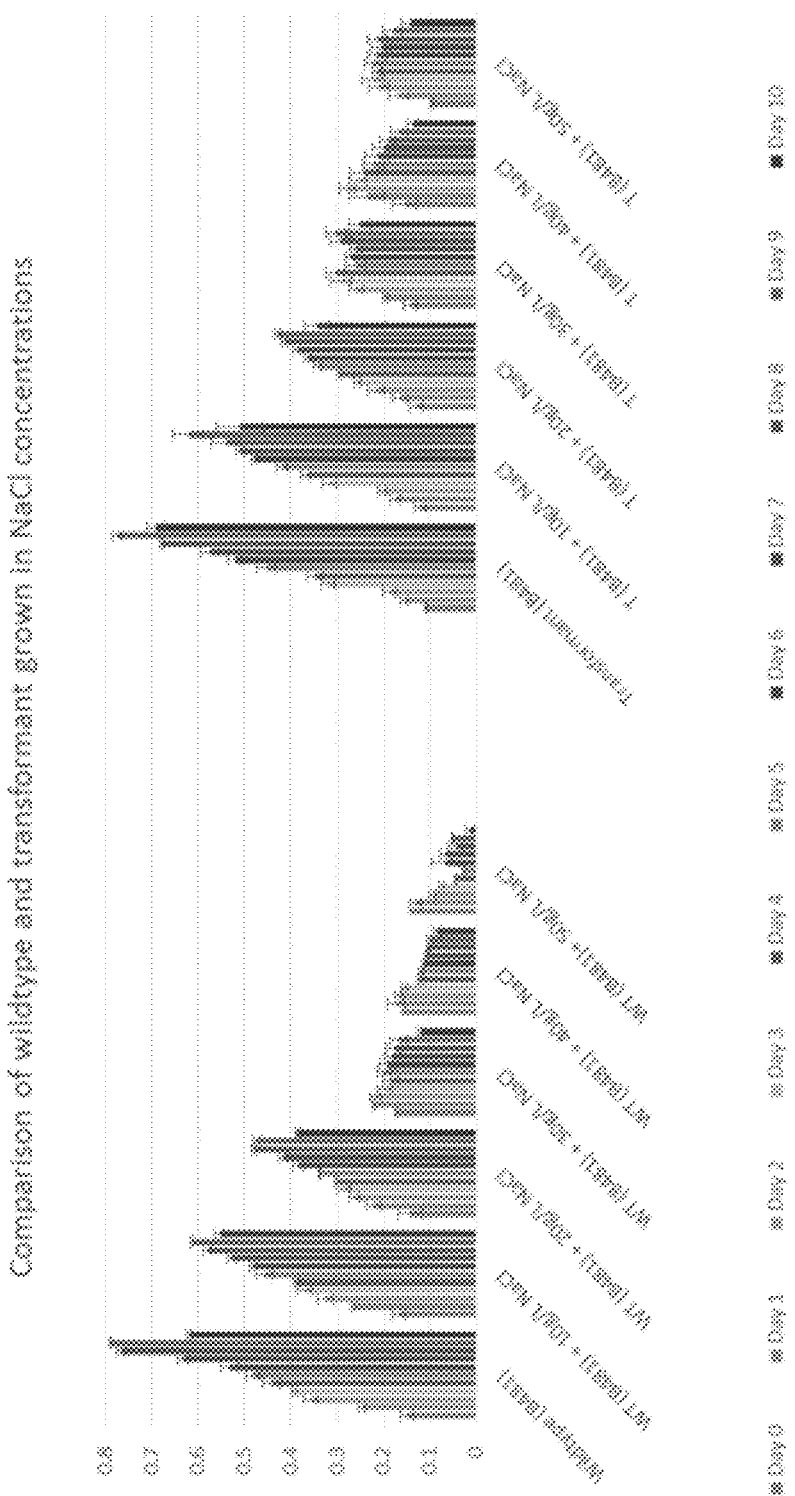
FIG. 11 shows the results of a growth experiment comparing wild type and transformant strains in media amended with various concentrations of sodium chloride.

*F. diplosiphon* B481-SD was capable of growth in liquid BG-11/HEPES medium at concentrations up to 50 g $L^{-1}$ NaCl (FIG. 11).

Figure 12:
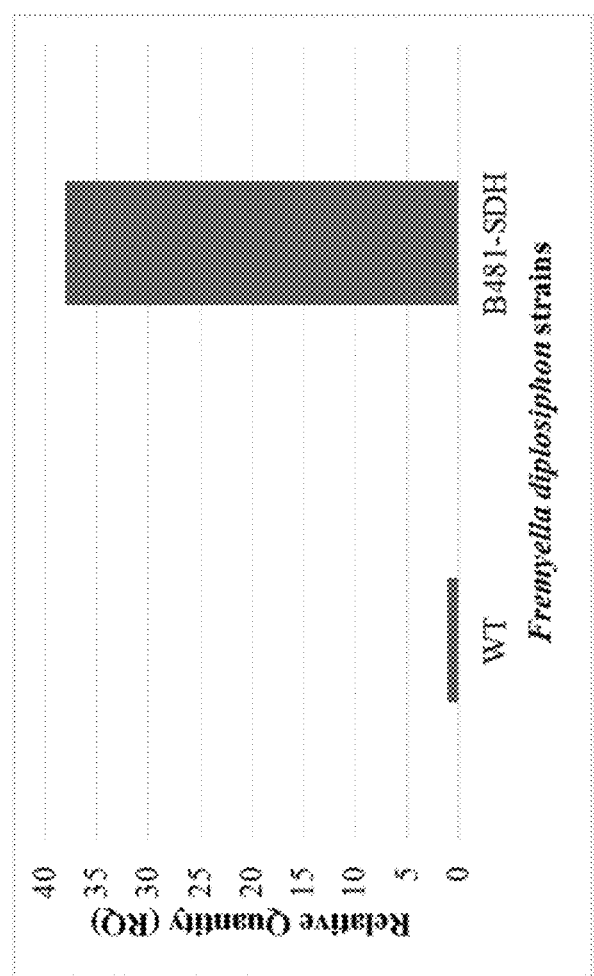
FIG. 12 shows relative quantification (RQ) of sterol desaturase transcript levels in *Fremyella diplosiphon* wild type (WT) and halotolerant transformant (B481-SDH).

Selection of the transformant was conducted at high salt content (40 g $L^{-1}$ NaCl). The resultant strain was named B481-SDH. RT-PCR shows B481-SDH transcript levels were 38-fold higher at 40 g $L^{-1}$ NaCl compared to WT (See FIG. 12).

SEQ. ID. NO. 1

LOCUS    Seq1[Fremyella 1314 bp mRNA linear BCT 10-MAY-2018

DEFINITION   diplosiphon] UTEX B481 F. diplosiphon Sterol desaturase mRNA, complete cds.

-continued

```
ACCESSION   Seq1[Fremyella

VERSION

KEYWORDS    .

SOURCE      Tolypothrix sp. PCC 7601 (Fremyella diplosiphon CCAP 1429/1)

ORGANISM    Tolypothrix sp. PCC 7601
            Bacteria; Cyanobacteria; Nostocales; Tolypothrichaceae;
            Tolypothrix.

REFERENCE   1 (bases 1 to 1314)

AUTHORS     Sitther, V., Gharaie Fathabad, S., Sigamani Arumanayagam, A. and
            Tabatabai, B.

TITLE       Overexpression of sterol desaturase gene in Fremyella diplosiphon

JOURNAL     Unpublished

REFERENCE   2 (bases 1 to 1314)

AUTHORS     Sitther, V., Gharaie Fathabad, S., Sigamani Arumanayagam, A. and
            Tabatabai, B.

TITLE       Direct Submission

JOURNAL     Submitted (09-MAY-2018) Biology, Morgan State Univer-
            sity, 1700 East
            Cold Spring Lane, Baltimore, MD 21251, United States COMMENT     Bankit Comment: ALT EMAIL: sogha1@morgan.edu.
            Bankit Comment: TOTAL # OF SEQS: 1.
            ##Assembly-Data-START##
            Sequencing Technology :: Sanger dideoxy sequencing
            ##Assembly-Data-END##

FEATURES    Location/Qualifiers
source      1 . . . 1314
            /organism = "Tolypothrix sp. PCC 7601"
            /mol type = "mRNA"
            /strain - "UTEX B481"
            /isolation source = "Freshwater"
            /db xref= "taxon: 1188"
            /note = "[cultured bacterial source]"

gene        1..1314
            /gene = "Sterol desaturase"
            /note = "Increase lipid content"

CDS         1 . . . 1314
            /gene = "Sterol desaturase"
            /note = "[intronless gene]; Increase lipid content; Lipid
            enhancement"
            /codon_start = 1
            /transl_table = 11
            /product = "Sterol desaturase"

1    ttgactttg  acttcttcat  agcgggacta  gcgctgataa  aaaccgagta  cagaaaaatt 61    acgatgaatg  ttttagcaca  aagctgggct  gagattgcgg  ctcaattaca  gataaattgg 121    aatctggtaa  atacctgctt  gcagtttgct  agttggggat  tagtctcgct  gttgttggta 181    gagatagtga  gagatagcta  tcatgctttg  tgtcactatg  tcccctcgct  tggtaaatgg 241    cataataagc  accacatggc  gtatcgccgc  gatttatcgg  tagtttcttt  aaaaatttac 301    caagagtctc  agttatacaa  tgatattgtc  gagtcaacgc  tactggttgt  agtttttgact 361    gtgatggctt  tactgctaca  gcaatggggc  ttttggttgg  gagtagtcta  tgctttcacc 421    tttttatatg  gcgcgtcccg  gcgataattt  ctcggtaaaa  ttgatacaga  ttacactcac 481    ctccccgggc  cattagaaac  tattccctcg  gtttggtggg  taaatcgttc  ttaccactgg 541    cgacatcatt  ttgatgatgt  taacgccat   tacagtggtg  tgttttccttt  agtagatacg 601    gtattgggaa  caggtttatc  tcttaaaggt  aaaaccattg  ctttaactgg  tgcttccggt
```

-continued

```
  661   gctttagggc aagcattgac tgctgaattg attaaaaata atgccaaggt agtagcctta 721   actaccaatc ccgaaaaact acagcctcaa gaaaagctaa ctgtaattgc ttgggaattg 781   ggtaaggaag cagagttaaa agctgcttta gagaaagttg atattttgat tatcaatcac 841   ggtgtcaatg tctacgctaa ccgcacctca gaagcaattg agtcttctta tgaggtgaat 901   acttttttcta cattgcggtt gatggatata ttttttggcaa ccgttaccgg gccgcaatcc 961   aaagcaacta agaaatttg ggttaacact tccgaagctg aagtatctcc ggctttaagt 1021   cctctttatg aactcagtaa acgcgctatc ggagatattg ttaccctcaa gcgtttggat 1081   ggggattgta taattcgcaa gttaattctg ggccgtttta agagtcaact taatccttat 1141   ggggtgatgt cagcgccgca agtagcccgt gcaattttgt ttttagcaaa gcgggacttc 1201   cgcaatatta ttgtgtccat caatcccctg acatatctgc tgtttccgtt gaaggaagtt 1261   agcacttggc tttactaccg aatctttagt aaaaaggttc aatctttgaa ctaa
//
```

---

The invention claimed is:

1. A recombinant *Fremyella diplosiphon* cyanobacterium comprising at least one plasmid, said at least one plasmid including at least one polynucleotide having the sequence of SEQ ID NO: 1 which encodes a sterol desaturase polypeptide.

2. The recombinant *Fremyella diplosiphon* cyanobacterium according to claim 1, having a higher salt tolerance as compared to wild-type *Fremyella diplosiphon* cyanobacterium.

* * * * *